US012582742B2

(12) United States Patent
Poetz et al.

(10) Patent No.: US 12,582,742 B2
(45) Date of Patent: Mar. 24, 2026

(54) PACKAGING SOLUTIONS

(71) Applicant: Bausch + Lomb Ireland Limited, Dublin (IE)

(72) Inventors: Katie L. Poetz, Scottsdale, AZ (US); Ivan M. Nuñez, Bluffton, SC (US); Analuz Mark, Spencerport, NY (US); Grace Bennett, Scottsville, NY (US); Robert Steffen, Naples, FL (US); Andrew J. Hoteling, Ontario, NY (US); Michelle Piotrowski, Rochester, NY (US); Brendan Shannon, Rochester, NY (US); Keyla Cubi, Tampa, FL (US); Alana Ingham, Hilton, NY (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 888 days.

(21) Appl. No.: 17/689,380

(22) Filed: Mar. 8, 2022

(65) Prior Publication Data

US 2022/0288270 A1 Sep. 15, 2022

Related U.S. Application Data

(60) Provisional application No. 63/159,881, filed on Mar. 11, 2021.

(51) Int. Cl.

*A61L 12/08* (2006.01)
*A61L 2/04* (2006.01)
*A61L 12/14* (2006.01)

(52) U.S. Cl.

CPC ............... *A61L 12/086* (2013.01); *A61L 2/04* (2013.01); *A61L 12/14* (2013.01); *A61L 2202/23* (2013.01)

(58) Field of Classification Search

None

See application file for complete search history.

(56) References Cited

U.S. PATENT DOCUMENTS 3,408,429 A 10/1968 Wichterle
3,660,545 A 5/1972 Wichterle
4,113,224 A 9/1978 Clark et al.
4,136,250 A 1/1979 Mueller et al.
4,153,641 A 5/1979 Deichert et al.
4,197,266 A 4/1980 Clark et al.
4,555,732 A 11/1985 Tuhro
4,740,533 A 4/1988 Su et al.
4,910,277 A 3/1990 Bambury et al.
4,954,587 A 9/1990 Mueller
5,010,141 A 4/1991 Mueller
5,034,461 A 7/1991 Lai et al.
5,070,215 A 12/1991 Bambury et al.
5,079,319 A 1/1992 Mueller
5,260,000 A 11/1993 Nandu et al.
5,271,876 A 12/1993 Ibar
5,310,779 A 5/1994 Lai
5,321,108 A 6/1994 Kunzler et al.
5,358,995 A 10/1994 Lai et al.
5,387,662 A 2/1995 Kunzler et al.
5,449,729 A 9/1995 Lai
5,512,205 A 4/1996 Lai
5,610,252 A 3/1997 Bambury et al.
5,616,757 A 4/1997 Bambury et al.
5,708,094 A 1/1998 Lai et al.
5,710,302 A 1/1998 Kunzler et al.
5,714,557 A 2/1998 Kunzler et al.
5,908,906 A 6/1999 Kunzler et al.
2008/0113002 A1* 5/2008 Yedgar .................... A61P 27/02 424/429
2008/0141628 A1* 6/2008 Lang ...................... A61L 12/04 53/425
2014/0102917 A1* 4/2014 Mori ...................... C08K 3/32 516/203

(Continued)

FOREIGN PATENT DOCUMENTS

CN 1328573 A 12/2001
CN 1390606 A 1/2003
CN 101677957 A 3/2010

(Continued)

OTHER PUBLICATIONS

Shante, Carole E. et al., "Chemical modifications of hyaluronic acid for the synthesis of derivatives for a broad range of biomedical applications," Carbohydrate Polymers, 2011, 85, pp. 469-489.
Shante, Carole E. et al., "Improvement of hyaluronic acid enzymatic stability by the grafting of amino-acids," Carbohydrate Polymers, 2012, 87. pp. 2211-2216.
Lai, Yu-Chin, "The Role of Bulky Polysiloxanylalkyl Methacryates in Polyurethane-Polysiloxane Hydrogels," Journal of Applied Polymer Science, 1996, pp. 1193-1199, vol. 60.

(Continued)

*Primary Examiner* — Ali Soroush
*Assistant Examiner* — Afua Bamfoaa Boateng
(74) *Attorney, Agent, or Firm* — Michael E. Carmen; John E. Thomas

(57) ABSTRACT

A packaging system for the storage of an ophthalmic device is disclosed. The packaging system includes a sealed container containing one or more unused ophthalmic devices immersed in an aqueous packaging solution that includes one or more conjugated glycosaminoglycans having a polymer backbone having a reactive functional moiety conjugated to an amine group having one or more moieties that inhibit and/or prevent one or more of oxidation and hydrolytic degradation of the polymer backbone during use in the eye; wherein the aqueous packaging solution has an osmolality of at least about 150 mOsm/kg, a pH of about 6 to about 9 and is sterilized.

22 Claims, No Drawings

(56) References Cited

U.S. PATENT DOCUMENTS

2015/0306237 A1 10/2015 Gurney et al.

FOREIGN PATENT DOCUMENTS

| | | | |
|---|---|---|---|
| CN | 103638040 | A | 3/2014 |
| CN | 112312791 | A | 2/2021 |
| JP | 2002529550 | A | 9/2002 |
| JP | 2006502988 | A | 1/2006 |
| JP | 2016141769 | A | 8/2016 |
| JP | 2022548996 | A | 11/2022 |
| WO | 9631792 | A1 | 10/1996 |
| WO | 2011148116 | A2 | 12/2011 |
| WO | 2020222914 | A1 | 11/2020 |
| WO | 2021053057 | A1 | 3/2021 |
| WO | PCT/EP2022/056058 | | 6/2022 |

OTHER PUBLICATIONS

Japanese Office Action for Japanese Application No. 2023-555185 dated Jul. 31, 2025, 4 pages.

Chinese Office Action for Chinese Application No. 202280020427.0 dated Nov. 13, 2025, 13 pages.

* cited by examiner

PACKAGING SOLUTIONS

PRIORITY CLAIM

The present application claims priority to U.S. Provisional Patent Application Ser. No. 63/159,881, entitled "Packaging Solutions," filed Mar. 11, 2021, the content of which is incorporated by reference herein in its entirety.

BACKGROUND

Blister-packs and glass vials are typically used to individually package each soft contact lens for sale to a customer. Saline or deionized water is commonly used to store the lens in the blister-packs. Because lens material may tend to stick to itself and to the lens package, packaging solutions for blister-packs have sometimes been formulated with various components to reduce or eliminate lens folding and sticking.

SUMMARY

In accordance with an illustrative embodiment, a packaging system for the storage of an ophthalmic device comprises a sealed container containing one or more unused ophthalmic devices immersed in an aqueous packaging solution comprising one or more conjugated glycosaminoglycans having a polymer backbone comprising a reactive functional moiety conjugated to an amine group comprising one or more moieties that inhibit and/or prevent one or more of oxidation and hydrolytic degradation of the polymer backbone during use in the eye; wherein the aqueous packaging solution has an osmolality of at least about 150 mOsm/kg, a pH of about 6 to about 9 and is sterilized.

In accordance with another illustrative embodiment, a packaging system for the storage of an ophthalmic device comprises a sealed container containing one or more unused ophthalmic devices immersed in an aqueous packaging solution comprising a reaction product of (a) one or more glycosaminoglycans having a polymer backbone comprising a reactive functional moiety, (b) an amine group comprising one or more moieties that inhibit and/or prevent one or more of oxidation and hydrolytic degradation of the polymer backbone during use in the eye, and (c) one or more coupling agents; wherein the aqueous packaging solution has an osmolality of at least about 150 mOsm/kg, a pH of about 6 to about 9 and is sterilized.

In accordance with yet another illustrative embodiment, a method of preparing a packaging system comprising a storable, sterile ophthalmic device is provided, the method comprising: (a) providing an ophthalmic device; (b) immersing the ophthalmic device in an aqueous packaging solution comprising one or more conjugated glycosaminoglycans having a polymer backbone comprising a reactive functional moiety conjugated to an amine group comprising one or more moieties that inhibit and/or prevent one or more of oxidation and hydrolytic degradation of the polymer backbone during use in the eye; wherein the aqueous packaging solution has an osmolality of at least about 150 mOsm/kg and a pH in the range of about 6 to about 9; (c) packaging the aqueous packaging solution and the ophthalmic device in a manner preventing contamination of the device by microorganisms; and (d) sterilizing the packaged solution and the ophthalmic device.

DETAILED DESCRIPTION

The illustrative embodiments described herein are directed to packaging systems for the storage of ophthalmic devices intended for direct contact with body tissue or body fluid, e.g., direct contact in the eye. It is highly desirable that an ophthalmic device such as a contact lens be as comfortable as possible for wearers. Manufacturers of contact lenses are continually working to improve the comfort of the lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

Glycosaminoglycans (GAGs) are a group of polysaccharides built of repeating disaccharide units. Due to high polarity and water affinity, they can be found in many systems of human bodies. For example, GAGs occur on the surface of cells and in the extracellular matrix of animal organisms such as skin, cartilage, and lungs.

GAGs each have a chemical structure including a repeating basal disaccharide structure consisting of uronic acid and hexosamine and being optionally sulfated to various degrees. GAGs are mainly classified, depending on the disaccharides constituting them, into three groups: a first group of compounds composed of chondroitin sulfate or dermatan sulfate, a second group of compounds composed of heparan sulfate or heparin, and a third group of hyaluronic acid compounds. For example, the compounds composed of chondroitin sulfate or dermatan sulfate consist of a disaccharide: uronic acid (glucuronic acid or iduronic acid) ($\beta 1 \rightarrow 3$) N-acetylgalactosamine, the compounds composed of heparan sulfate or heparin consist of a disaccharide: uronic acid (glucuronic acid or iduronic acid) ($\beta 1 \rightarrow 4$)N-acetylglucosamine, and the hyaluronic acid consists of a disaccharide: glucuronic acid ($\beta 1 \rightarrow 3$)N-acetylglucosamine. In addition, the structure is highly diverse due to a combination with modification by sulfation.

These GAGs are known as biological materials having both physicochemical properties derived from characteristic viscoelasticity and biological properties mediated by interactions with various functional proteins, depending on the molecular size and the sulfation pattern. However, GAGs such as hyaluronic acid having too low of a molecular weight can break down into fragments making it less lubricious and causing discomfort in the eye.

To overcome these and other problems associated with GAGs such as hyaluronic acid having too low of a molecular weight and breaking down into fragments, illustrative embodiments described herein are directed to conjugating the GAGs such as hyaluronic acid or a salt thereof disclosed herein with an amine group comprising one or more moieties that inhibit oxidation of the polymer backbone of the GAG during use in the eye. It is believed that the conjugated GAG will be less susceptible to oxidation such as environmentally induced oxidation, thereby improving overall stability and comfort in the eye. In addition, illustrative embodiments described herein are further directed to conjugating the GAGs disclosed herein with an amine group comprising one or more moieties that prevent hydrolytic degradation of the polymer backbone during use in the eye. It is believed that the conjugated GAG will have improved stability toward enzymatic degradation.

Accordingly, these and other illustrative embodiments provide an improved packaging system for ophthalmic devices such as a contact lens such that the lens would be more lubricious and comfortable to wear in actual use thereby allowing for extended wear of the lens without irritation or other adverse effects to the cornea.

Thus, in a non-limiting illustrative embodiment, an aqueous packaging solution for use in a packaging system for ophthalmic devices as disclosed herein containing one or more conjugated glycosaminoglycans having a polymer backbone comprising a reactive functional moiety conjugated to an amine group comprising one or more moieties that inhibit oxidation and/or prevent hydrolytic degradation of the polymer backbone during use in the eye is believed to provide improved lubricity and/or wettability of an ophthalmic device. The ophthalmic device will therefore be more comfortable to wear in actual use and allow for extended wear of the lens without irritation or other adverse effects to the cornea. Hydrophilic and/or lubricious surfaces of the ophthalmic devices herein such as contact lenses substantially prevent or limit the adsorption of tear lipids and proteins on, and their eventual absorption into, the lenses, thus preserving the clarity of the contact lenses. This, in turn, preserves their performance quality thereby providing a higher level of comfort to the wearer.

As used herein, the term "ophthalmic device" refers to devices that reside in or on the eye. These lenses can provide optical correction, wound care, drug delivery, diagnostic functionality or cosmetic enhancement or effect or a combination of these properties. Representative examples of such devices include, but are not limited to, soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. Any material known to produce an ophthalmic device including a contact lens can be used herein.

The ophthalmic devices can be any material known in the art capable of forming an ophthalmic device as described above. In one embodiment, an ophthalmic device includes devices which are formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl(meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1,3-dioxol. Representative examples of suitable bulk materials include, but are not limited to, lotrafilcon A, neofocon, pasifocon, telefocon, silafocon, fluorsilfocon, paflufocon, silafocon, elastofilcon, fluorofocon or Teflon® AF materials, such as Teflon® AF 1600 or Teflon® AF 2400 which are copolymers of about 63 to about 73 mol % of perfluoro-2,2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, an ophthalmic device includes a device which is formed from material hydrophilic per se, since reactive groups, e.g., carboxy, carbamoyl, sulfate, sulfonate, phosphate, amine, ammonium or hydroxy groups, are inherently present in the material and therefore also at the surface of an ophthalmic device manufactured therefrom. Such devices are formed from materials known in the art and include, by way of example, polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, polymacon, tefilcon, methafilcon, deltafilcon, bufilcon, phemfilcon, ocufilcon, focofilcon, etafilcon, hefilcon, vifilcon, tetrafilcon, perfilcon, droxifilcon, dimefilcon, isofilcon, mafilcon, nelfilcon, atlafilcon and the like. Examples of other suitable bulk materials include balafilcon A, hilafilcon A, alphafilcon A, bilafilcon B and the like.

In another embodiment, an ophthalmic device includes a device which is formed from materials which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed from a bulky silicone monomer (e.g., tris(trimethylsiloxy)silylpropyl methacrylate, commonly known as "TRIS" monomer), methacrylate end-capped poly (dimethylsiloxane)prepolymer, or silicones having fluoroalkyl side groups (polysiloxanes are also commonly known as silicone polymers).

Hydrogels in general are a well-known class of materials that comprise hydrated, crosslinked polymeric systems containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer can function as a crosslinking agent (a crosslinker being defined as a monomer having multiple polymerizable functionalities) or a separate crosslinker may be employed. Silicone hydrogels typically have a water content between about 10 to about 80 weight percent.

Representative examples of useful hydrophilic monomers include, but are not limited to, amides such as N,N-dimethylacrylamide and N,N-dimethylmethacrylamide; cyclic lactams such as N-vinyl-2-pyrrolidone; and (meth)acrylated poly(alkene glycols), such as poly(diethylene glycols) of varying chain length containing monomethacrylate or dimethacrylate end caps. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art. For example, 2-hydroxyethylmethacrylate (HEMA) is a well-known hydrophilic monomer that may be used in admixture with the aforementioned hydrophilic monomers.

The monomer mixtures may also include a second device-forming monomer including a copolymerizable group and a reactive functional group. The copolymerizable group is preferably an ethylenically unsaturated group, such that this device-forming monomer copolymerizes with the hydrophilic device-forming monomer and any other device-forming monomers in the initial device-forming monomer mixture. Additionally, the second monomer can include a reactive functional group that reacts with a complementary reactive group of the copolymer which is the reaction product of one or more polymerizable polyhydric alcohols and one or more polymerizable fluorine-containing monomers. In other words, after the device is formed by copolymerizing the device-forming monomer mixture, the reactive functional groups provided by the second device-forming monomers remain to react with a complementary reactive moiety of the copolymer.

In one embodiment, reactive groups of the second device-forming monomers include epoxide groups. Accordingly, second device-forming monomers are those that include both an ethylenically unsaturated group (that permits the monomer to copolymerize with the hydrophilic device-forming monomer) and the epoxide group (that does not react with the hydrophilic device-forming monomer but remains to react with a copolymer, e.g., the reaction product of one or more polymerizable polyhydric alcohols and one or more polymerizable fluorine-containing monomers). Suitable second device-forming monomers include, for example, glycidyl methacrylate, glycidyl acrylate, glycidyl vinylcarbonate, glycidyl vinylcarbamate, and 4-vinyl-1-cyclohexene-1,2-epoxide.

As mentioned, one class of ophthalmic device substrate materials are silicone hydrogels. In this case, the initial device-forming monomer mixture further comprises a silicone-containing monomer. Applicable silicone-containing monomeric materials for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of suitable materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

Representative examples of applicable silicone-containing monomers include bulky polysiloxanylalkyl(meth) acrylic monomers. An example of a bulky polysiloxanylalkyl(meth)acrylic monomer is represented by the structure of Formula (I):

(I)

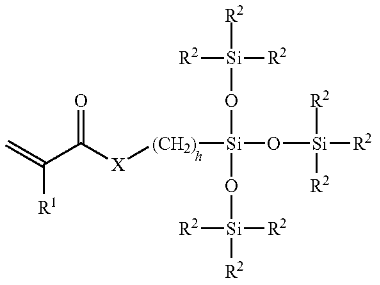

wherein X denotes —O— or —NR— wherein R denotes hydrogen or a $C_1$ to $C_4$ alkyl; $R^1$ denotes hydrogen or methyl; each $R^2$ independently denotes a lower alkyl radical such as a $C_1$ to $C_4$ alkyl radical, a phenyl radical or a group represented by

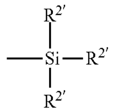

wherein each $R^{2'}$ independently denotes a lower alkyl radical such as a $C_1$ to $C_4$ alkyl radical, or a phenyl radical; and h is 1 to 10.

Examples of bulky monomers are methacryloxypropyl tris(trimethyl-siloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, for example, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris (trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicone-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae (II) and (III):

$$E(*D*A*D*G)_a*D*A*D*E'; \text{ or} \quad (II)$$

$$E(*D*G*D*A)_a*D*A*D*E'; \text{ or} \quad (III)$$

wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A independently denotes a divalent polymeric radical of Formula (IV):

(IV)

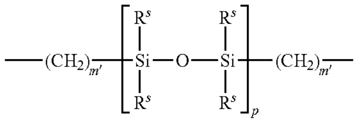

wherein each $R^5$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula (V):

(V)

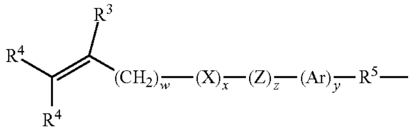

wherein: $R^3$ is hydrogen or methyl;

$R^4$ is hydrogen, an alkyl radical having 1 to 6 carbon atoms, or a —CO—Y—$R^6$ radical wherein Y is —O—, —S— or —NH—;

$R^5$ is a divalent alkylene radical having 1 to about 10 carbon atoms;

$R^6$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

In one embodiment, a silicone-containing urethane monomer is represented by Formula (VI):

In another embodiment, a silicone hydrogel material comprises (in bulk, that is, in the monomer mixture that is copolymerized) about 5 to about 50 percent, or from about 10 to about 25, by weight of one or more silicone macromonomers, about 5 to about 75 percent, or about 30 to about 60 percent, by weight of one or more polysiloxanylalkyl (meth)acrylic monomers, and about 10 to about 50 percent, or about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates. The silane macromonomer may be a silicone-containing vinyl carbonate or vinyl carbamate or a polyurethane-polysiloxane having one or more hard-soft-hard blocks and end-capped with a hydrophilic monomer.

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. Also, the use of silicone-containing monomers having certain fluorinated side groups, i.e., —$(CF_2)$—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates according to the embodiments disclosed herein that have been disclosed in various publications and are being continuously developed for use in contact lenses and other medical devices can also be used. For example, an ophthalmic device can be formed from at least a cationic monomer such as cationic silicone-containing monomer or cationic fluorinated silicone-containing monomers.

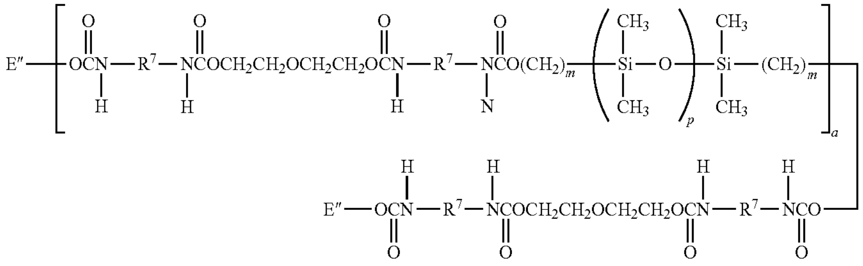

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

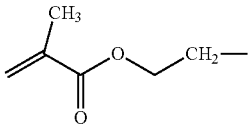

Contact lenses disclosed herein can be manufactured employing various conventional techniques, to yield a shaped article having the desired posterior and anterior lens surfaces. Spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

As one skilled in the art will readily appreciate, ophthalmic device surface functional groups of the ophthalmic device may be inherently present at the surface of the device. However, if the ophthalmic device contains too few or no functional groups, the surface of the device can be modified by known techniques or conventional functionalization with groups such as —OH, —$NH_2$ or —$CO_2H$. Suitable ophthalmic device surface functional groups of the ophthalmic device include a wide variety of groups well known to the skilled artisan. Representative examples of such functional groups include, but are not limited to, hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. In one embodiment, the ophthalmic device surface functional groups of the ophthalmic device are amino groups and/or hydroxy groups.

Next, the resulting ophthalmic device such as a contact lens will be immersed in an aqueous packaging solution and stored in a packaging system according to illustrative embodiments described herein. Generally, a packaging system for the storage of an ophthalmic device includes at least a sealed container containing one or more unused ophthalmic devices immersed in an aqueous packaging solution. In one illustrative embodiment, the sealed container is a hermetically sealed blister-pack, in which a concave well containing an ophthalmic device such as a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

In one illustrative embodiment, the aqueous packaging solution for use in the packaging system disclosed herein will contain one or more conjugated glycosaminoglycans (GAG) having a polymer backbone comprising a reactive functional moiety conjugated to an amine group comprising one or more moieties that inhibit and/or prevent one or more of oxidation and hydrolytic degradation of the polymer backbone during use in the eye. In one illustrative embodiment, the one or more conjugated glycosaminoglycans are present in the aqueous packaging solution in an amount ranging from about 0.05 to about 5 weight percent, based on the total weight of the aqueous packaging solution. In another illustrative embodiment, the one or more conjugated glycosaminoglycans are present in the aqueous packaging solution in an amount ranging from about 0.1 to about 3 weight percent, based on the total weight of the aqueous packaging solution. In another illustrative embodiment, the one or more conjugated glycosaminoglycans are present in the aqueous packaging solution in an amount ranging from about 0.01 weight percent to about 0.1 weight percent, based on the total weight of the aqueous packaging solution.

A GAG is one molecule with many alternating subunits. In general, GAGs are represented by the formula A-B-A-B-A-B, where A is uronic acid and B is an amino sugar that may or may not be either O- or N-sulfated, where the A and B units can be heterogeneous with respect to epimeric content or sulfation. Any natural or synthetic polymer containing uronic acid can be used. Other GAGs are sulfated at different sugars. There are many different types of GAGs having commonly understood structures such as, for example, chondroitin sulfate (e.g., chondroitin 4- and 6-sulfates), heparan, heparin sulfate, heparosan, dermatan, dermatan sulfate, hyaluronic acid or a salt thereof, e.g., sodium hyaluronate or potassium hyaluronate, keratan sulfate, and other disaccharides such as sucrose, lactulose, lactose, maltose, trehalose, cellobiose, mannobiose and chitobiose. Glycosaminoglycans can be purchased from Sigma, and many other biochemical suppliers such as HTL Biotechnology (France). In one illustrative embodiment, the GAG is hyaluronic acid. In one embodiment, the GAG is chondroitin sulfate.

The GAGs will have a reactive functional group in the polymer backbone for conjugating with the amine group comprising one or more moieties that inhibit and/or prevent one or more of oxidation and hydrolytic degradation of the polymer backbone during use in the eye. Suitable reactive functional groups in the polymer backbone of the GAGs include, for example, carboxylate-containing groups, hydroxyl-containing groups, silicone hydride groups, sulfur-containing groups such as thiols and other groups including polymerizable functionalities such as allylic, vinylic, acrylate, methacrylate, methacrylamide, etc. In one illustrative embodiment, the reactive functional group in the polymer backbone of the GAG is a carboxylate-containing group for conjugating with the amine group comprising one or more moieties that inhibit and/or prevent one or more of oxidation and hydrolytic degradation of the polymer backbone during use in the eye. In addition, the sugar rings of the GAGs can be opened to form aldehydes for further functionalization.

In an illustrative embodiment, a GAGs for use herein can have a weight average molecular weight ranging from about 10,000 to about 3,000,000 Daltons (Da) in which the lower limit is from about 10,000, about 20,000, about 30,000, about 40,000, about 50,000, about 60,000, about 70,000, about 80,000, about 90,000, or about 100,000, and the upper limit is about 200,000, about 300,000, about 400,000, about 500,000, about 600,000, about 700,000, about 800,000, about 900,000, about 1,000,000, or about up to 2,800,000 Da, where any of the lower limits can be combined with any of the upper limits. In one illustrative embodiment, a GAGs for use herein can have a weight average molecular weight ranging from about 1,000,000 to about 3,000,000 Da.

Hyaluronic acid is a well-known, naturally occurring, water soluble biodegradable polymer composed of two alternatively linked sugars, D-glucuronic acid and N-acetylglucosamine, linked via alternating β-(1,4) and β-(1,3) glycosidic bonds. Hyaluronic acid is a non-sulfated GAG. The polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from Seikagaku Company, Clear Solutions Biotech, Inc., Pharmacia Inc., Sigma Inc., HTL Biotechnology, Contipro and Bloomage Biotechnology Corporation, and many other suppliers. Hyaluronic acid has repeating units of the structure represented by the following formula:

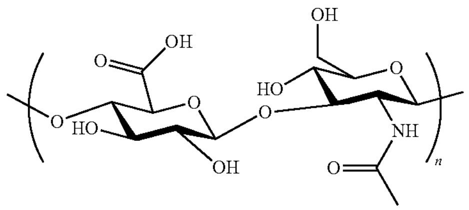
.

Accordingly, the repeating units in hyaluronic acid can be as follows:

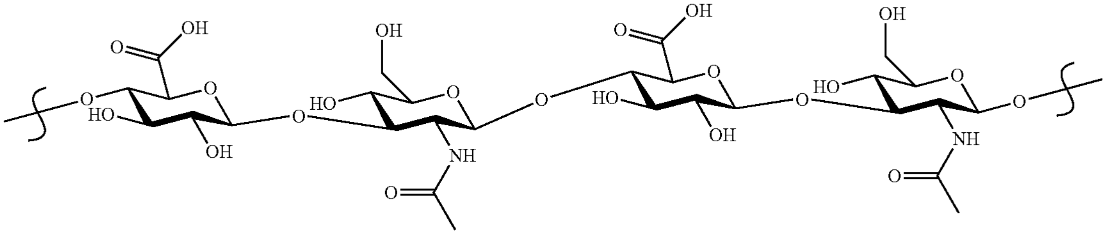

β-D-Glucuronic acid N-Acetyl-β-D-Glucosamine β-D-Glucuronic acid N-Acetyl-β-D-Glucosamine In general, hyaluronic acid or a salt thereof can have from about 2 to about 1,500,000 disaccharide units. In one embodiment, hyaluronic acid or a salt thereof can have a weight average molecular weight ranging from about 10,000 to about 3,000,000 Da in which the lower limit is from about 10,000, about 20,000, about 30,000, about 40,000, about 50,000, about 60,000, about 70,000, about 80,000, about 90,000, or about 100,000, and the upper limit is about 200,000, about 300,000, about 400,000, about 500,000, about 600,000, about 700,000, about 800,000, about 900,000, about 1,000,000, or about up to 2,800,000 Da, where any of the lower limits can be combined with any of the upper limits. In one illustrative embodiment, a hyaluronic acid or salt thereof for use herein can have a weight average molecular weight ranging from about 1,000,000 to about 3,000,000 Da.

Chondroitin sulfate is a linear sulfated polysaccharide composed of repeating β-D-glucuronic acid (GlcA) and N-acetyl-β-D-galactosamine (GalNAc) units arranged in the sequence by GlcA-β(1,3)-GalNAc-β(1,4) glycosidic bonds. In one embodiment, chondroitin sulfate has one or more repeating units of the structure represented by the following formula:

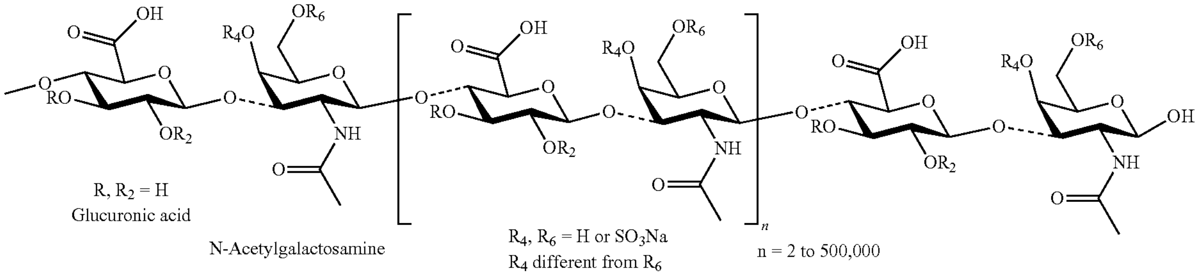

$R, R_2 = H$
Glucuronic acid

N-Acetylgalactosamine $R_4, R_6 = H$ or $SO_3Na$
$R_4$ different from $R_6$ n = 2 to 500,000

In one illustrative embodiment, chondroitin sulfate has repeating units of the structure represented by the following formula:

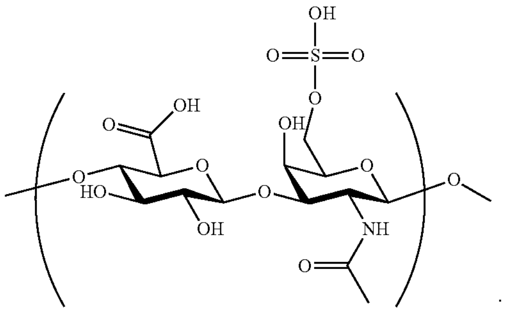

In general, chondroitin sulfate can have from about 2 to about 1,500,000 repeating units. In one embodiment, chondroitin sulfate can have a weight average molecular weight ranging from about 10,000 to about 3,000,000 Da in which the lower limit is from about 5,000, 10,000, about 20,000, about 30,000, about 40,000, about 50,000, about 60,000, about 70,000, about 80,000, about 90,000, or about 100,000, and the upper limit is about 200,000, about 300,000, about 400,000, about 500,000, about 600,000, about 700,000, about 800,000, about 900,000, about 1,000,000, or about 3,000,000 Da where any of the lower limits can be combined with any of the upper limits or any of the upper limits can be combined with any of the upper limits. In one illustrative embodiment, a chondroitin sulfate for use herein can have a weight average molecular weight ranging from about 1,000,000 to about 3,000,000 Da.

In one illustrative embodiment, dermatan sulfate has repeating units of the structure represented by the following formula:

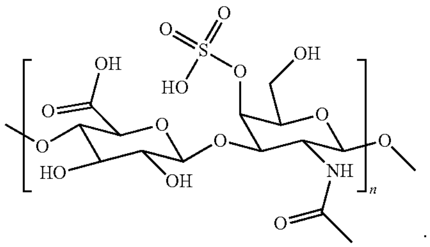

In general, dermatan sulfate can have from about 2 to about 1,500,000 repeating units. In one embodiment, dermatan sulfate can have a weight average molecular weight ranging from about 1,000 to about 2,000,000 Da in which the lower limit is from about 1,000, 5,000, 10,000, about 20,000, about 30,000, about 40,000, about 50,000, about 60,000, about 70,000, about 80,000, about 90,000, or about 100,000, and the upper limit is about 200,000, about 300,000, about 400,000, about 500,000, about 600,000, about 700,000, about 800,000, about 900,000, about 1,000,000, or about 2,000,000 Da where any of the lower limits can be combined with any of the upper limits or any of the upper limits can be combined with any of the upper limits. In one illustrative embodiment, a dermatan sulfate for use herein can have a weight average molecular weight ranging from about 1,000 to about 1,000,000 Da.

In one illustrative embodiment, heparin and heparin sulfate has repeating units of the structure represented by the following formula:

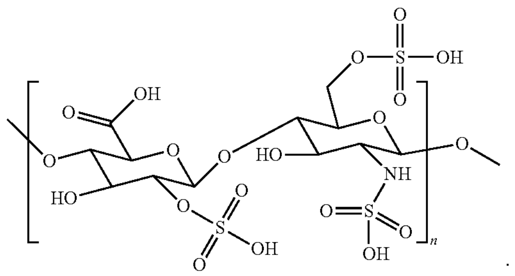

In general, heparin and heparin sulfate can have from about 2 to about 1,500,000 repeating units. In one embodiment, heparin and heparin sulfate can have a weight average molecular weight ranging from about 1,000 to about 3,000,000 Da in which the lower limit is from about 1,000, 5,000, 10,000, about 20,000, about 30,000, about 40,000, about 50,000, about 60,000, about 70,000, about 80,000, about 90,000, or about 100,000, and the upper limit is about 40,000, 100,000, 200,000, about 300,000, about 400,000, about 500,000, about 600,000, about 700,000, about 800,000, about 900,000, about 1,000,000, or about 3,000,000 Da where any of the lower limits can be combined with any of the upper limits or any of the upper limits can be combined with any of the upper limits. In one illustrative embodiment, heparin and heparin sulfate for use herein can have a weight average molecular weight ranging from about 2,000 to about 40,000 Da.

In one illustrative embodiment, keratan sulfate has repeating units of the structure represented by the following formula:

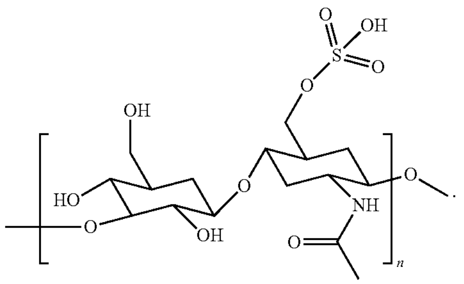

In general, keratan sulfate can have from about 2 to about 1,500,000 repeating units. In one embodiment, keratan sulfate can have a weight average molecular weight ranging from about 10,000 to about 3,000,000 Da in which the lower limit is from about 5,000, 10,000, about 20,000, about 30,000, about 40,000, about 50,000, about 60,000, about 70,000, about 80,000, about 90,000, or about 100,000, and the upper limit is about 100,000, 200,000, about 300,000, about 400,000, about 500,000, about 550,000, 600,000, about 700,000, about 800,000, about 900,000, about 1,000,000, or about 3,000,000 where any of the lower limits can be combined with any of the upper limits or any of the upper limits can be combined with any of the upper limits. In one illustrative embodiment, keratan sulfate for use herein can have a weight average molecular weight ranging from about 15,000 to about 550,000 Da.

The reactive functional group in the polymer backbone of the GAG is conjugated with an amine group comprising one or more moieties that inhibit and/or prevent one or more of oxidation and hydrolytic degradation of the polymer backbone during use in the eye to form the conjugated GAG. In one illustrative embodiment, an amine group comprising one or more moieties that inhibit and/or prevent one or more of oxidation and hydrolytic degradation of the polymer backbone during use in the eye is an amine group comprising a moiety that inhibits oxidation of the polymer backbone during use in the eye. In another illustrative embodiment, an amine group comprising one or more moieties that inhibit and/or prevent one or more of oxidation and hydrolytic degradation of the polymer backbone during use in the eye is an amine group comprising one or more moieties that inhibit hydrolytic degradation of the polymer backbone during use in the eye. In another illustrative embodiment, an amine group comprising one or more moieties that inhibit and/or prevent one or more of oxidation and hydrolytic degradation of the polymer backbone during use in the eye is an amine group comprising one or more moieties that inhibit both oxidation and hydrolytic degradation of the polymer backbone during use in the eye.

In illustrative non-limiting embodiments, one or more moieties of the amine group that inhibit and/or prevent oxidation of the polymer backbone during use in the eye include hydroxyl-containing groups as defined herein. In illustrative non-limiting embodiments, one or more moieties of the amine group that inhibit and/or prevent hydrolytic degradation of the polymer backbone during use in the eye can include ester-containing groups as defined herein. In illustrative non-limiting embodiments, one or more moieties of the amine group that inhibit and/or prevents oxidation of the polymer backbone during use in the eye can include hydroxyl-containing groups and ester-containing groups.

In an illustrative embodiment, a suitable amine group comprising one or more moieties that inhibit and/or prevent one or more of oxidation and hydrolytic degradation of the polymer backbone during use in the eye for conjugating with the reactive functionality of the GAG is represented by a structure of Formula (VII):

(VII)

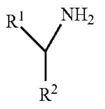

wherein $R^1$ is hydrogen, a substituted or unsubstituted alkyl group, a substituted or unsubstituted cycloalkyl group, a substituted or unsubstituted cycloalkylalkyl group, a substituted or unsubstituted cycloalkenyl group, a substituted or unsubstituted aryl group, a substituted or unsubstituted arylalkyl group, a substituted or unsubstituted ester group or a substituted or unsubstituted alkoxy group, and $R^2$ is a substituted or unsubstituted hydroxyl-containing hydrocarbyl group.

Representative examples of alkyl groups for use herein include, by way of example, a straight or branched alkyl chain radical containing carbon and hydrogen atoms of from 1 to about 30 carbon atoms or from 1 to about 12 carbon atoms, or from 1 to about 6 carbon atoms, or from 1 to 3 carbon atoms with or without unsaturation, to the rest of the molecule, e.g., methyl, ethyl, n-propyl, 1-methylethyl (isopropyl), n-butyl, n-pentyl, methylene, ethylene, etc., and the like.

Representative examples of cycloalkyl groups for use herein include, by way of example, a substituted or unsubstituted non-aromatic mono or multicyclic ring system of about 3 to about 30 carbon atoms, or from 3 to about 6 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4, 4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 4 to about 30 carbon atoms, or from 3 to about 6 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms, or from 3 to about 6 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 6 to about 30 carbon atoms, or from about 6 to about 12 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., $—CH_2C_6H_5$, $—C_2H_4C_6H_5$ and the like, wherein the aryl group can optionally contain one or more heteroatoms, e.g., O and N, and the like.

Representative examples of ester groups for use herein include, by way of example, a carboxylic acid ester having 2 to 20 carbon atoms and the like.

Representative examples of alkoxy groups for use herein include, by way of example, an alkoxy group having 1 to 20 carbon atoms and the like.

Suitable hydrocarbyl groups for the substituted or unsubstituted hydroxyl-containing hydrocarbyl group include any $C_2$ to about $C_{30}$ hydrocarbyl groups including, by way of example, substituted or unsubstituted aliphatic (e.g., alkyl or alkenyl) substituents, substituted or unsubstituted alicyclic (e.g., cycloalkyl, cycloalkenyl) substituents and substituted or unsubstituted aromatic substituents as described above. The number of hydroxyl moieties on the hydrocarbyl group can vary widely depending on the hydrocarbyl group and can range from 1 to about 8 hydroxyl groups. For example, a benzyl substituent can have from 1 to 5 hydroxyl groups.

In an illustrative embodiment, a suitable amine group comprising one or more moieties that inhibit and/or prevent one or more of oxidation and hydrolytic degradation of the polymer backbone during use in the eye for conjugating with the reactive functionality of the GAG is represented by a structure of Formula (VIII):

(VIII)

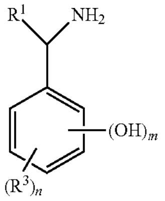

wherein $R^1$ has the aforestated meanings, $R^3$ is independently from one another a substituted or unsubstituted alkyl group, a substituted or unsubstituted cycloalkyl group, a substituted or unsubstituted cycloalkylalkyl group, a substituted or unsubstituted cycloalkenyl group, a substituted or unsubstituted aryl group, and a substituted or unsubstituted arylalkyl group, m is 0 to 5 or 1 to 5 and n is 0 to 4. In one illustrative embodiment, representative examples of the foregoing amine group include 4-hydroxylbenzeneamine, methyl 4-hydroxylbenzeneamine, and ethyl 4-hydroxylbenzeneamine.

In an illustrative embodiment, a suitable amine group comprising one or more moieties that inhibit and/or prevent one or more of oxidation and hydrolytic degradation of the polymer backbone during use in the eye for conjugating with the reactive functionality of the GAG is represented by a structure of Formula (IX):

(IX)

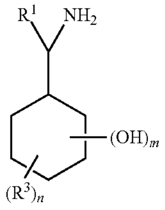

wherein $R^1$, $R^3$, m and n have the aforestated meanings. In one illustrative embodiment, a representative example of the foregoing amine group includes glucosamine.

In one illustrative embodiment, a suitable amine group comprising one or more moieties that inhibit and/or prevent one or more of oxidation and hydrolytic degradation of the polymer backbone during use in the eye for conjugating with the GAG includes, for example, one or more amino acids. Suitable amino acids include, for example, L-Lysine, L-Valine, L-Tryptophan, L-Phenylalanine, L-methionine, L-Leucine, L-Threonine, L-Isoleucine, L-Arginine, L-Histidine, L-Tyrosine, L-Tyrosine tert-butyl ester, L-Carnitine, L-Serine, L-Glutamine, Aspartic Acid, L-Proline, L-Proline methyl ester, L-Glycine, Taurine, L-Cysteine, Gamma-aminobutyric acid (GABA), L-Alanine, L-Glutamic acid, Threonine, Tyramine and salts thereof.

The conjugated glycosaminoglycans disclosed herein can be obtained by conjugating the amine group comprising one or more moieties that inhibit and/or prevent one or more of oxidation and hydrolytic degradation of the polymer backbone during use in the eye to the reactive functional moiety in the polymer backbone of the glycosaminoglycan. For example, in one illustrative embodiment, an amine reactive end group of the amine group comprising one or more moieties that inhibit and/or prevent one or more of oxidation and hydrolytic degradation of the polymer backbone during use in the eye can be conjugated onto a carboxylic acid group in the polymer backbone of the glycosaminoglycan. In one illustrative embodiment, the amine group comprising one or more moieties that inhibit and/or prevent one or more of oxidation and hydrolytic degradation of the polymer backbone during use is conjugated onto the reactive functional moiety in the polymer backbone of the glycosaminoglycan by covalent bonding.

The conjugated GAGs disclosed herein comprising one or more moieties that inhibit and/or prevent one or more of oxidation and hydrolytic degradation of the polymer backbone during use in the eye include conjugated GAGs having a variety of molecular weights, structures or geometries (e.g., branched, linear, and the like). In an illustrative embodiment, the weight average molecular weight of the conjugated GAG may range from about 100,000 Da to about 3,000,000 Da. In one illustrative embodiment, a weight average molecular weight of conjugated GAG can be greater than about 100,000 Da, or greater than about 1,000,000 Da, or greater than about 2,000,000 Da. In another illustrative embodiment, a weight average molecular weight of conjugated GAG can be less than about 3,000,000 Da, or less than about 1,000,000 Da, or less than about 500,000 Da. As one skilled in the art can appreciate, any of the lower limits can be combined with any of the upper limits or any of the upper limits can be combined with any of the upper limits.

In one illustrative embodiment, the conjugated glycosaminoglycans can be obtained by reacting the one or more glycosaminoglycans with the amine group under suitable conjugation conditions in the presence of one or more coupling agents. Suitable conjugation conditions for the reaction include, for example, a temperature of about 15° C. to about 30° C. for a time period of about 6 hours to about 30 hours. In one illustrative embodiment, suitable conjugation conditions for the reaction include, for example, a temperature of about 20° C. to about 25° C. for a time period of about 16 hours to about 24 hours.

In one illustrative embodiment, the one or more glycosaminoglycans can be added to the reaction mixture in an amount ranging from about 0.2 to about 5 weight percent, based on the total weight of the reaction mixture. In one illustrative embodiment, the one or more glycosaminoglycans can be added to the reaction mixture in an amount ranging from about 1 to about 2 weight percent, based on the total weight of the reaction mixture.

In one illustrative embodiment, an amine group comprising one or more moieties that inhibit and/or prevent one or more of oxidation and hydrolytic degradation of the polymer backbone during use in the eye can be added to the reaction mixture in an amount ranging from about 0.05 to about 1 weight percent, based on the total weight of the reaction mixture. In one illustrative embodiment, an amine group comprising one or more moieties that inhibit and/or prevent one or more of oxidation and hydrolytic degradation of the polymer backbone during use in the eye can be added to the reaction mixture in an amount ranging from about 0.08 to about 0.5 weight percent, based on the total weight of the reaction mixture.

Suitable coupling agents include, for example, carbodiimide compounds, succinimide compounds and the like. In one embodiment, a carbodiimide compound can be those represented by a compound having the formula:

$$RN{=}C{=}NR'$$

wherein R and R', which are the same or different, are a hydrocarbyl group such as a $C_1$-$C_8$ alkyl or a $C_6$-$C_{30}$ aryl group. In one embodiment the alkyl groups have from 1 to 6 carbon atoms. The alkyl groups may be linear, cyclic or branched, and can be interrupted by heteroatoms, such S, N or O. In particular, the alkyl groups can be substituted by an amine group, such as, for example, —$N^{+}H(CH_3)_2$. Representative examples of suitable alkyl groups having from 1 to 8 carbon atoms include methyl, ethyl, propyl, isopropyl, t-butyl, isobutyl, n-butyl, pentyl, isopentyl, hexyl, heptyl, octyl, 2-ethylhexyl, 2-methylbutyl, 2-methylpentyl, 1-methylhexyl, 3-methylheptyl and the other isomeric forms thereof.

Suitable aryl groups include, for example, mono-, bi- or tri-cyclic aromatic hydrocarbon radicals. In one embodiment the aryl groups are monocyclic or bicyclic aromatic hydrocarbons containing from 6 to 18 carbon atoms. Representative examples of suitable aryl groups include phenyl, naphthyl and biphenyl groups.

In one illustrative embodiment, the carbodiimide compound is 1-ethyl-3-(3-dimethylaminopropyl) carbodiimide (EDC).

A suitable succinimide coupling agent for use herein include, for example, N-hydroxysuccinimide (NHS) and sulfo-N-hydroxysuccinimide (Sulfo-NHS).

In one illustrative embodiment, a coupling agent include 1-ethyl-3-(3-dimethylaminopropyl)carbodiimide (EDC)/N-hydroxysuccinimide (NHS) or EDC/hydroxybenzotriazole (HOBt) coupling at a pH of about 6.8 with about 1 to about 5 weight percent dissolved solids in water to form random copolymers or block copolymers.

In one embodiment, a carbodiimide coupling agent such as EDC can be added to the reaction mixture in an amount ranging from about 0.01 to about 20 weight percent, based on the total weight of the reaction mixture. In one embodiment, a succinimide coupling agent such as NHS is added to the reaction in an amount ranging from about 0.01 to about 20 weight percent, based on the total weight of the reaction mixture.

The packaging solutions described herein are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The packaging solution should also be sterile in that the absence of microbial contaminants in the product prior to release must be statistically demonstrated to the degree necessary for such products. The liquid media useful herein are selected to have no substantial detrimental effect on the lens being treated or cared for and to allow or even facilitate the present lens treatment or treatments. In one embodiment, the liquid media is aqueous-based. A particularly useful aqueous liquid medium is that derived from saline, for example, a conventional saline solution or a conventional buffered saline solution.

The pH of the packaging solutions should be maintained within the range of about 6 to about 9, or from about 6.5 to about 7.8. Suitable buffers may be added, such as boric acid, sodium borate, potassium citrate, citric acid, sodium bicarbonate, TRIS and various mixed phosphate buffers (including combinations of $Na_2HPO_4$, $NaH_2PO_4$ and $KH_2PO_4$) and mixtures thereof. Generally, buffers will be used in amounts ranging from about 0.05 to about 2.5 percent by weight of the solution. In one embodiment, buffers will be used in amounts ranging from about 0.1 to about 1.5 percent by weight of the solution. The packaging solutions disclosed herein preferably contain a borate buffer, containing one or more of boric acid, sodium borate, potassium tetraborate, potassium metaborate or mixtures of the same.

Typically, the packaging solutions are also adjusted with tonicity agents, to approximate the osmotic pressure of normal lacrimal fluids which is equivalent to a 0.9 percent solution of sodium chloride or 2.5 percent of glycerol solution. The packaging solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Suitable tonicity adjusting agents include, for example, sodium and potassium chloride, dextrose, calcium and magnesium chloride and the like and mixtures thereof. These tonicity adjusting agents are typically used individually in amounts ranging from about 0.01 to about 2.5% w/v. In one embodiment, the tonicity adjusting agents are used in amounts ranging from about 0.2 to about 1.5% w/v. The tonicity agent will be employed in an amount to provide a final effective osmotic value of at least about 150 mOsm/kg. In one embodiment, the tonicity adjusting agents are used in an amount to provide a final effective osmotic value of from about 150 to about 400 mOsm/kg. In one embodiment, the tonicity adjusting agents are used in an amount to provide a final effective osmotic value of from about 150 to about 350 mOsm/kg. In one embodiment, the tonicity adjusting agents are used in an amount to provide a final effective osmotic value of from about 160 to about 220 mOsm/kg.

If desired, one or more additional components can be included in the packaging solution. Such additional components are chosen to impart or provide at least one beneficial or desired property to the packaging solution. In general, the additional components may be selected from components which are conventionally used in one or more ophthalmic device care compositions. Suitable additional components include, for example, cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Suitable sequestering agents include, for example, disodium ethylene diamine tetraacetate, alkali metal hexametaphosphate, citric acid, sodium citrate and the like and mixtures thereof.

Suitable viscosity builders include, for example, hydroxyethyl cellulose, hydroxymethyl cellulose, polyvinyl pyrrolidone, polyvinyl alcohol and the like and mixtures thereof.

Suitable antioxidants include, for example, sodium metabisulfite, sodium thiosulfate, N-acetylcysteine, butylated hydroxyanisole, butylated hydroxytoluene and the like and mixtures thereof.

The method of packaging and storing an ophthalmic device such as a contact lens according to an illustrative embodiment includes at least packaging an ophthalmic device immersed in the aqueous packaging solution described above. The method may include immersing the ophthalmic device in an aqueous packaging solution prior to delivery to the customer/wearer, directly following manufacture of the contact lens. Alternately, the packaging and storing in the packaging solution may occur at an intermediate point before delivery to the ultimate customer (wearer) but following manufacture and transportation of the lens in a dry state, wherein the dry lens is hydrated by immersing the lens in the packaging solution. Consequently, a package for delivery to a customer may include a sealed container containing one or more unused contact lenses immersed in an aqueous packaging solution disclosed herein.

In one illustrative embodiment, the steps leading to the packaging system disclosed herein includes (1) molding an ophthalmic device in a mold comprising at least a first and second mold portion, (2) hydrating and cleaning the ophthalmic device in a container optionally comprising at least one of the mold portions, (3) introducing the aqueous packaging solution disclosed herein into the container with the ophthalmic device supported therein, and (4) sealing the container. In one illustrative embodiment, the method also includes the step of sterilizing the contents of the container. Sterilization may take place prior to, or most conveniently after, sealing of the container and may be affected by any suitable method known in the art, e.g., by autoclaving of the sealed container at temperatures of about 120° C. or higher.

The following examples are provided to enable one skilled in the art to practice the invention and are merely illustrative of the invention. The examples should not be read as limiting the scope of the invention as defined in the claims.

Example 1

Synthesis of 4-Hydroxylamine-Functionalized Hyaluronic Acid

Hyaluronic acid (Mw~909,200 Da) (300 mg ($3.23\times10^{-7}$ moles)) was dissolved in water (15 mL) overnight at room temperature. To the solution was added 1-Ethyl-3-(3-dimethylaminopropyl) carbodiimide (EDC) (0.11 g; 0.000481 moles) and N-hydroxysuccinimide (NHS) (0.07 g; 0.000481 moles) and stirred at room temperature. Next, 4-hydroxybenzylamine (0.02 g, 0.00024 moles) was added and stirred for 48 hours at room temperature. The 4-hydroxylamine-functionalized hyaluronic acid was purified through dialysis for two days, and isolated by freeze drying. Mass spectrometry determined that the 4-hydroxybenzylamine was conjugated to the hyaluronic acid. The synthesis of 4-hydroxylamine-functionalized hyaluronic acid is shown below.

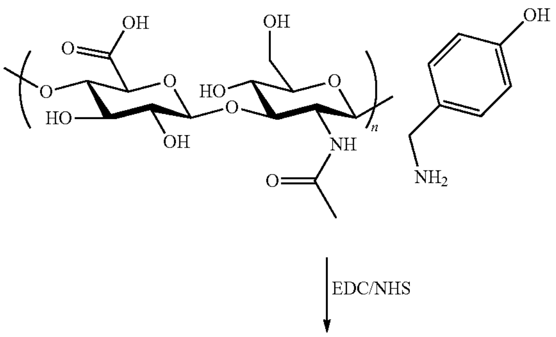

-continued

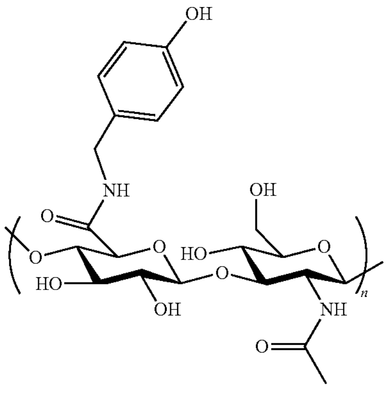

Example 2

Synthesis of L-Proline Methyl Ester Hydrochloride-Functionalized Hyaluronic Acid Hyaluronic acid (Mw~1,320,500 Da) (300 mg ($3.23\times10^{-7}$ moles)) was dissolved in water (15 mL) overnight at room temperature. To the solution was added EDC (0.09 g, 0.000481 moles) and NHS (0.05 g, 0.000481 moles) and stirred at room temperature. Next, L-Proline methyl ester hydrochloride (0.05 g, 0.00024 moles) was added and stirred for 48 hours at room temperature. Proline methyl ester hydrochloride-functionalized hyaluronic acid was purified through dialysis for two days, and isolated by freeze drying. Mass spectrometry determined that the L-Proline methyl ester hydrochloride was conjugated to the hyaluronic acid. The synthesis of L-Proline methyl ester hydrochloride-functionalized hyaluronic acid is shown below.

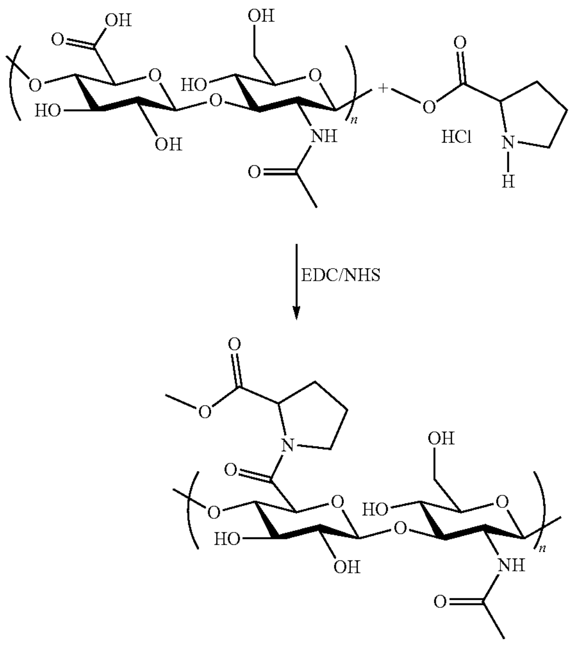

Example 3

Synthesis of Glucosamine-Functionalized Sodium Hyaluronate

Sodium hyaluronate (Mw~1,000,000) (1.0 g, 0.001 mmol) was dissolved in DI water (50 ml) in a media bottle rolling for 3 days. To the solution was added EDC (0.307 g, 1.6 mmol) and NHS (0.185 g, 1.6 mmol) and rolled for about 7 hours. Next, glucosamine (0.173 g, 0.8 mmol) was added and rolled for 4 days, diluted with water and dialyzed for 2 days. The material was freeze dried for 5 days and collected 0.90 g (90%) as a white solid. Mass spectrometry determined that the glucosamine was conjugated to the hyaluronic acid. The glucosamine-functionalized sodium hyaluronate is represented by the structure below.

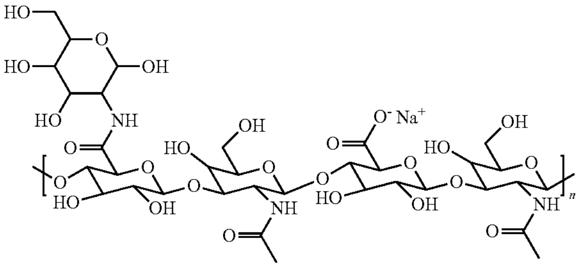

Example 4

Synthesis of Tyrosine-Functionalized Hyaluronic Acid

Hyaluronic acid (Mw~909,200 Da) (0.343 g, $3.23\times10^{-7}$ moles) was dissolved in distilled water (12 mL) overnight by rolling at room temperature. Tyrosine (0.06 g, $2.4\times10^{-4}$ moles), EDC (0.10 g, $4.8\times10^{-4}$ moles) and NHS (0.05 g, $4.8\times10^{-4}$ moles) were added to the reaction flask and rolled over several days at room temperature. The tyrosine-functionalized hyaluronic acid was purified with dialysis with a 3,500 kDa cutoff for three days by changing the water in the morning and at 4 pm each day. Mass spectrometry determined that the tyrosine was conjugated to the hyaluronic acid. The synthesis of tyrosine-functionalized hyaluronic acid is shown below.

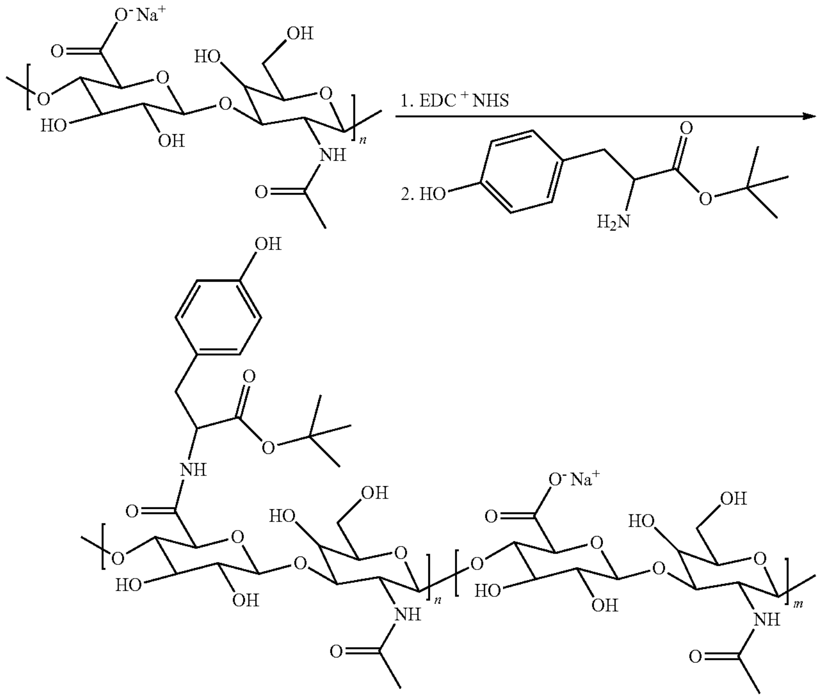

Example 5

Synthesis of Taurine-Functionalized Hyaluronic Acid

Hyaluronic acid (Mw~1,320,500 Da) (0.5 g, $1.3\times10^{-3}$ moles) of HA was dissolved in distilled water (60 mL) overnight at room temperature on a roller. Taurine (0.68 g; $5.4\times10^{-3}$ moles), EDC (0.5 g; $2.6\times10^{-3}$ moles), and NHS (0.32 g; $2.6\times10^{-3}$ moles) were added the following day to the media bottle and rolled overnight. The taurine-functionalized hyaluronic acid was purified via dialysis, and isolated by freeze drying. Mass spectrometry determined that the taurine was conjugated to the hyaluronic acid.

Example 6

Synthesis of Tyramine-Functionalized Hyaluronic Acid

Sodium hyaluronate (Mw~1,000,000) (1.0 g; 0.001 mmol) was dissolved in DI water (100 mls) in a media bottle rolling for 3 days. To the solution was added EDC (0.307 g, 1.6 mmol) and NHS (0.185 g, 1.6 mmol) and rolled for about 7 hours. Next, tyramine (0.110 g, 0.8 mmol) was added and rolled for 4 days. The solution was diluted with water and dialyzed for 2 days. The tyramine-functionalized hyaluronic acid was freeze dried for 5 days and collected 0.90 g (90%) as a white solid. Mass spectrometry determined that the tyramine was conjugated to the hyaluronic acid. The tyramine-functionalized hyaluronic acid is represented by the structure below.

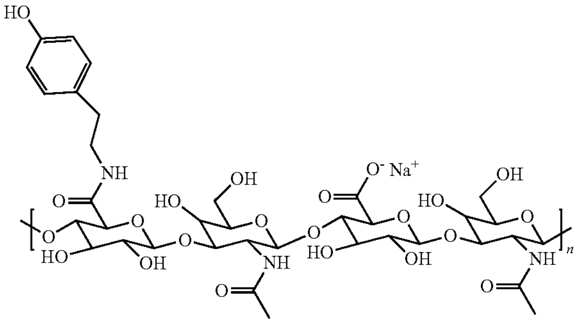

Example 7

Synthesis of Threonine-Functionalized Sodium Hyaluronate

Sodium hyaluronate (HA; Mw~1,000,000) (2.0 g, 0.002 mmol) was dissolved in DI water (200 mLs) in a media bottle (concentration=1.0%) and rolled for 3 days. To the solution was added EDC (0.615 g, 3.2 mmol) and NHS (0.369 g, 3.2 mmol) and rolled for about 5 hours. Next, threonine (0.339 g, 1.6 mmol) was added and rolled for 2.5 days. The solution was diluted with water (200 mLs) and then added Amberlite IR-120 $Na^+$ form (60 g) and rolled for 5 hours. The resin was filtered and rinsed with fresh DI water. The filtrate was placed in dialyzing tubes (MWCO 6-8K), dialyzed for 4 days and then freeze dried for 2 days. Mass spectrometry determined that the threonine was conjugated to the hyaluronic acid. The synthesis of threonine-functionalized sodium hyaluronate is shown below.

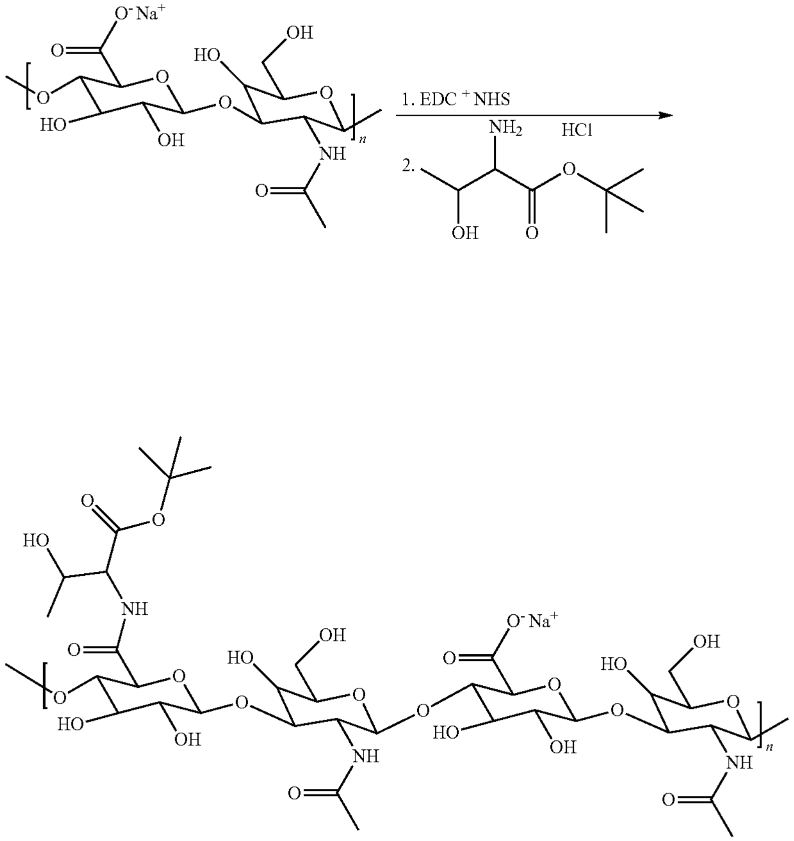

Example 8

Synthesis of Glycine-Functionalized Hyaluronic Acid

Hyaluronic acid (Mw~1,141,000 Da) (1.0 g, $1.0\times10^{-6}$ moles) was dissolved in distilled water (100 mL) overnight at room temperature. To the solution was added NHS (0.39 g, $3.4\times10^{-3}$ moles) and EDC (0.54 g, $2.8\times10^{-3}$ moles) and reacted for 4-5 hours. Next, glycine (0.16 g, $9.5\times10^{-4}$ moles) was added and rolled for a minimum of two days at room temperature. The crude reaction was treated with the cation exchange resin, Amberlite IR120 $Na^+$ for four hours. The resin was removed via filtration, and the glycine-functionalized hyaluronic acid was dialyzed for a minimum of two days. Following dialysis, the glycine-functionalized hyaluronic acid was lyophilized. Mass spectrometry determined that the glycine was conjugated to the hyaluronic acid. The synthesis of glycine-functionalized hyaluronic acid is shown below.

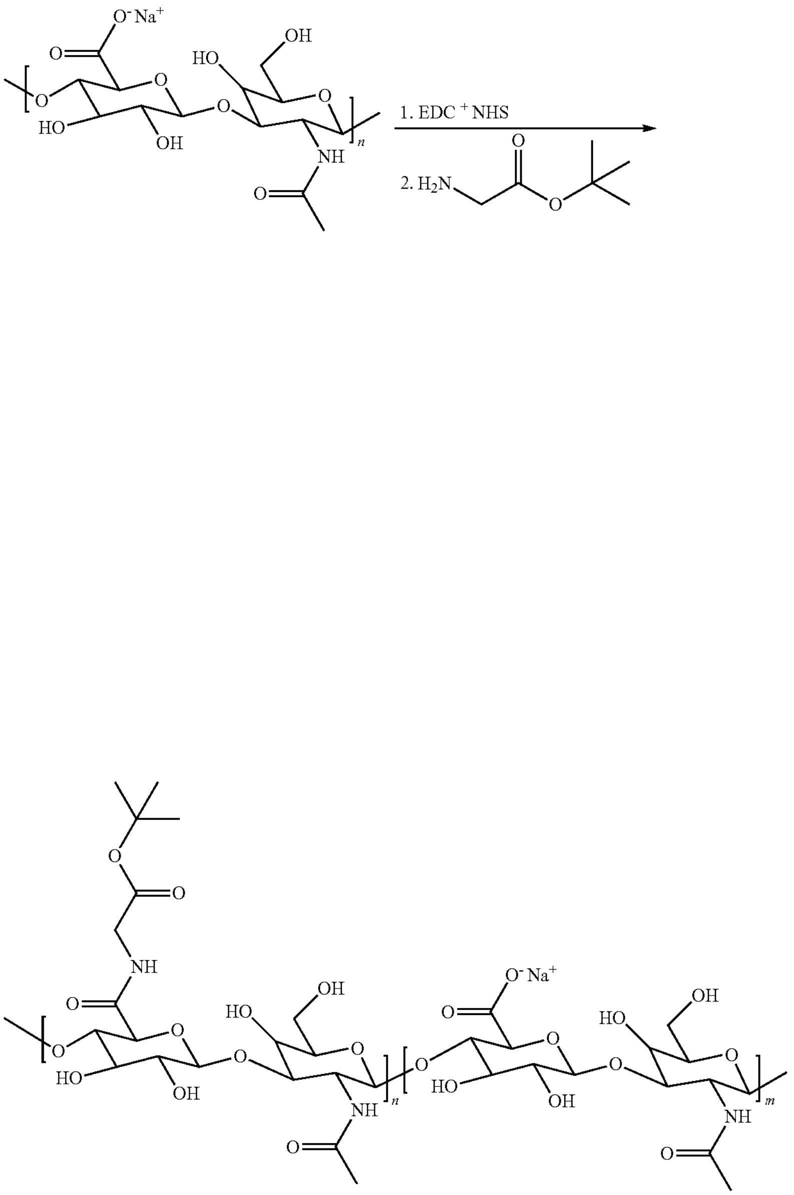

Example 9

Synthesis of L-Phenylalanine-Functionalized Hyaluronic Acid-Functionalized Hyaluronic Acid Sodium hyaluronate (Mw~1,000,003) (2.0 g, 0.002 mmol) was dissolved in DI water (200 mLs) in a media bottle (concentration=1.0%) and rolled for 3 days. To the solution was added EDC (0.615 g, 3.2 mmol) and NHS (0.369 g, 3.2 mmol) and rolled for about 6 hours. Next, L-phenylalanine t-butyl ester (0.413 g, 1.6 mmol) was added and rolled for 2.5 days. The solution was diluted with water (200 mLs) and then added Amberlite IR-120 $Na^+$ form (50 g) and rolled for 6 hours. The resin was filtered and rinsed with fresh DI water. The filtrate was placed in dialyzing tubes (MWCO 6-8K), dialyzed for 5 days and then freeze dried for 2 days. Mass spectrometry determined that the L-phenylalanine was conjugated to the hyaluronic acid. The synthesis of L-phenylalanine-functionalized hyaluronic acid is shown below.

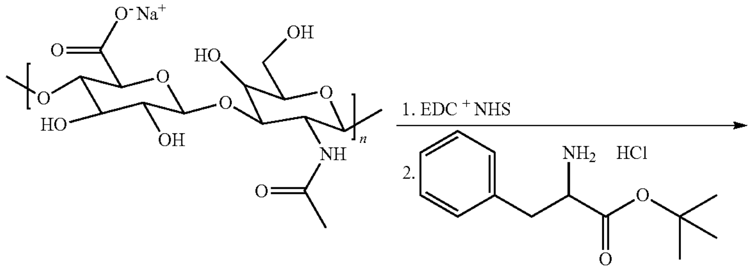

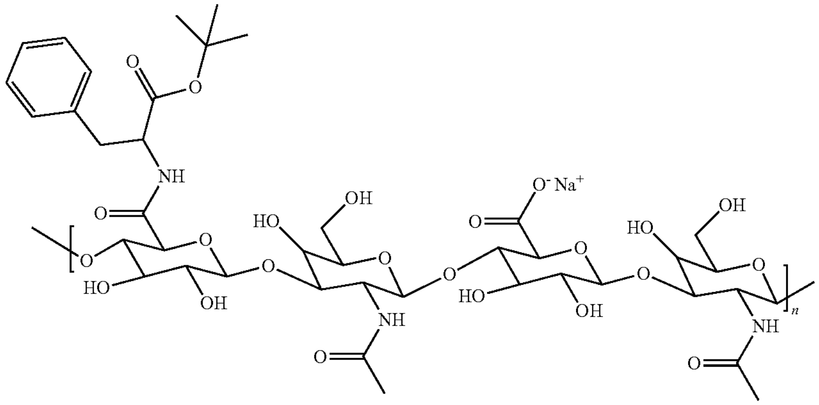

Example 10

Synthesis of 4-Hydroxybenzylamine-Functionalized Hyaluronic Acid

A 50 mL-single neck round bottom flask equipped temperature probe was charged with HA in HPLC water, then added MeCN while stirring HA aqueous solution. While stirring slowly added NMM to the reaction flask, then cooled solution using an ice/water bath. Once internal temperature reached 4° C. then added CDMT to the reaction mixture. Once addition was finished, allowed mixture to stir at room temperature for 1 hour. Then added 4-hydroxybenzylamine while stirring, then allowed reaction to stir at room temperature for 48 hours. The solution was then submitted to dialysis (6.5 kDa $M_w$ cutoff) against deionized water. Dialyzed solution was then freeze dried. Mass spectrometry determined that the 4-hydroxybenzylamine was conjugated to the hyaluronic acid.

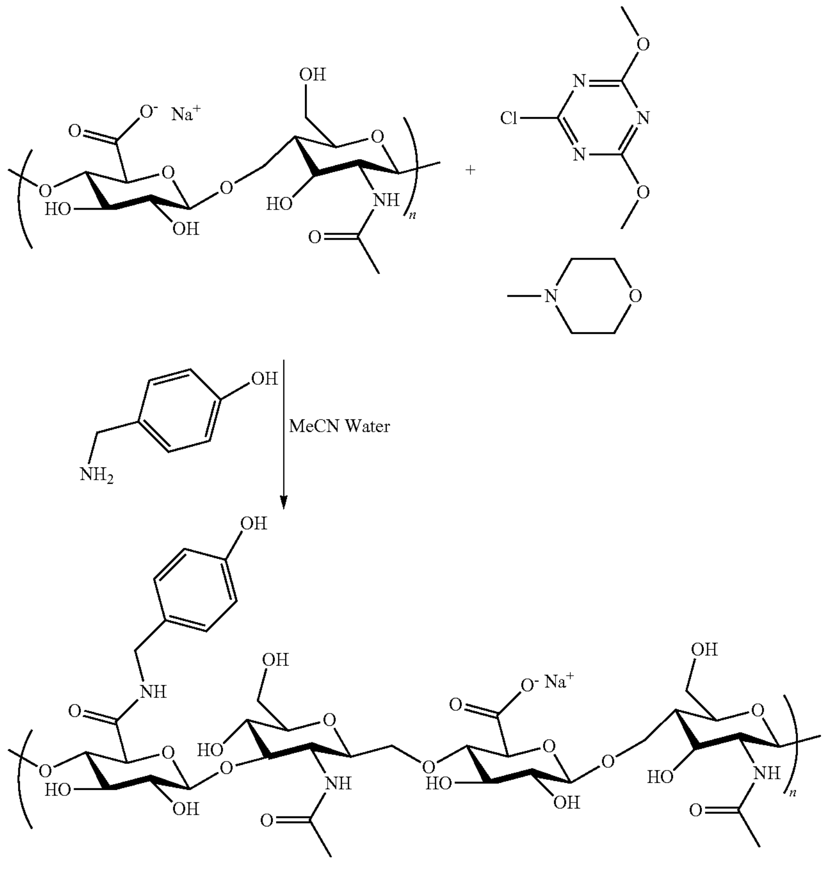

Example 11

An aqueous packaging solution was made by mixing the following components, listed in Table 1 at amounts per weight.

TABLE 1

| Ingredient | % w/w |
|---|---|
| Potassium Chloride (KCl) | 0.70 |
| Dibasic Sodium Phosphate, anhydrous | 0.032 |

TABLE 1-continued

| Ingredient | % w/w |
|---|---|
| Monobasic Sodium Phosphate, anhydrous | 0.0093 |
| Poloxamer 181 | 0.02 |
| Poloxamer 1107 (TH 07) | 0.55 |
| Glycerol, Anhydrous, USP | 0.90 |
| Erythritol | 0.90 |
| Example 1 | 0.04 |
| Purified Water | Q.S. to 100% w/w |

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present formulations and are disclosed herein just as if each and every such sub-combination was individually and explicitly disclosed herein.

It will be understood that various modifications may be made to the embodiments disclosed herein. Therefore, the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A packaging system for the storage of an ophthalmic device comprising:

a sealed container containing one or more unused ophthalmic devices immersed in an aqueous packaging solution comprising one or more conjugated glycosaminoglycans having a polymer backbone comprising a reactive functional moiety conjugated to an amine group of an end terminal amino acid comprising one or more moieties comprising one or more of an unconjugated hydroxyl-containing group and an unconjugated ester-containing group;

wherein the aqueous packaging solution has an osmolality of at least about 150 mOsm/kg, a pH of about 6 to about 9 and is sterilized.

2. The packaging system of claim 1, wherein the one or more unused ophthalmic devices are one or more unused contact lenses.

3. The packaging system of claim 1, wherein the one or more conjugated glycosaminoglycans are selected from the group consisting of chondroitin, chondroitin sulfate, dermatan, dermatan sulfate, heparin, heparan sulfate, hyaluronan and hyaluronic acid or a salt thereof.

4. The packaging system of claim 1, wherein the aqueous packaging solution comprises about 0.01 weight percent to about 0.1 weight percent, based on the total weight of the aqueous packaging solution, of the one or more conjugated glycosaminoglycans.

5. The packaging system of claim 1, wherein the aqueous packaging solution further comprises one or more of a poloxamer and a poloxamine.

6. The packaging system of claim 1, wherein the aqueous packaging solution further comprises one or more additives selected from the group consisting of a buffer agent, a tonicity adjusting agent, a cleaning agent, a wetting agent, a nutrient agent, a sequestering agent, a viscosity builder, a contact lens conditioning agent, an antioxidant, and mixtures thereof.

7. The packaging system of claim 1, wherein the sealed container is heat sterilized subsequent to sealing of the container and the aqueous packaging solution does not contain an effective disinfecting amount of a disinfecting agent or a germicide compound.

8. A packaging system for the storage of an ophthalmic device comprising a sealed container containing one or more unused ophthalmic devices immersed in an aqueous packaging solution comprising one or more conjugated glycosaminoglycans of a reaction product of (a) one or more glycosaminoglycans having a polymer backbone comprising a reactive functional moiety, (b) an end terminal amino acid comprising an amine group and one or more moieties comprising one or more of a hydroxyl-containing group and an ester-containing group, and (c) one or more coupling agents selected from a carbodiimide compound, a succinimide compound or a combination thereof; wherein the aqueous packaging solution has an osmolality of at least about 150 mOsm/kg, a pH of about 6 to about 9 and is sterilized.

9. The packaging system of claim 8, wherein the one or more glycosaminoglycans are selected from the group consisting of chondroitin, chondroitin sulfate, dermatan, dermatan sulfate, heparin, heparan sulfate, hyaluronan and hyaluronic acid or a salt thereof.

10. The packaging system of claim 8, wherein the aqueous packaging solution comprises about 0.01 weight percent to about 0.1 weight percent, based on the total weight of the aqueous packaging solution, of the one or more conjugated glycosaminoglycans.

11. The packaging system of claim 1, wherein the amino acid is selected from the group consisting of L-Lysine, L-Valine, L-Tryptophan, L-Phenylalanine, L-methionine, L-Leucine, L-Threonine, L-Isoleucine, L-Arginine, L-Histidine, L-Tyrosine, L-Tyrosine tert-butyl ester, L-Carnitine, L-Serine, L-Glutamine, Aspartic Acid, L-Proline, L-Proline methyl ester, L-Glycine, Taurine, L-Cysteine, Gamma-aminobutyric acid (GABA), L-Alanine, L-Glutamic acid, Threonine, Tyramine and salts thereof.

12. The packaging system of claim 8, wherein the amino acid is selected from the group consisting of L-Lysine, L-Valine, L-Tryptophan, L-Phenylalanine, L-methionine, L-Leucine, L-Threonine, L-Isoleucine, L-Arginine, L-Histidine, L-Tyrosine, L-Tyrosine tert-butyl ester, L-Carnitine, L-Serine, L-Glutamine, Aspartic Acid, L-Proline, L-Proline methyl ester, L-Glycine, Taurine, L-Cysteine, Gamma-aminobutyric acid (GABA), L-Alanine, L-Glutamic acid, Threonine, Tyramine and salts thereof.

13. The packaging system of claim 8, wherein the one or more unused ophthalmic devices are one or more unused contact lenses.

14. The packaging system of claim 8, wherein the one or more conjugated glycosaminoglycans are a conjugated hyaluronic acid or a salt thereof.

15. The packaging system of claim 14, wherein the amino acid is selected from the group consisting of L-Lysine, L-Valine, L-Tryptophan, L-Phenylalanine, L-methionine, L-Leucine, L-Threonine, L-Isoleucine, L-Arginine, L-Histidine, L-Tyrosine, L-Tyrosine tert-butyl ester, L-Carnitine, L-Serine, L-Glutamine, Aspartic Acid, L-Proline, L-Proline methyl ester, L-Glycine, Taurine, L-Cysteine, Gamma-aminobutyric acid (GABA), L-Alanine, L-Glutamic acid, Threonine, Tyramine and salts thereof.

16. The packaging system of claim 8, wherein the hydroxyl-containing group is an OH group and the ester-containing group is a methyl ester.

17. The packaging system of claim 8, wherein the aqueous packaging solution comprises about 0.01 weight percent to about 0.1 weight percent, based on the total weight of the aqueous packaging solution, of the one or more conjugated glycosaminoglycans, wherein the one or more conjugated glycosaminoglycans are a conjugated hyaluronic acid or a salt thereof.

18. The packaging system of claim 1, wherein the one or more conjugated glycosaminoglycans are a conjugated hyaluronic acid or a salt thereof.

19. The packaging system of claim 18, wherein the amino acid is selected from the group consisting of L-Lysine, L-Valine, L-Tryptophan, L-Phenylalanine, L-methionine, L-Leucine, L-Threonine, L-Isoleucine, L-Arginine, L-Histidine, L-Tyrosine, L-Tyrosine tert-butyl ester, L-Carnitine, L-Serine, L-Glutamine, Aspartic Acid, L-Proline, L-Proline methyl ester, L-Glycine, Taurine, L-Cysteine, Gamma-aminobutyric acid (GABA), L-Alanine, L-Glutamic acid, Threonine, Tyramine and salts thereof.

20. The packaging system of claim 1, wherein the unconjugated hydroxyl-containing group is an OH group and the unconjugated ester-containing group is a methyl ester.

21. The packaging system of claim 1, wherein the aqueous packaging solution comprises about 0.01 weight percent to about 0.1 weight percent, based on the total weight of the aqueous packaging solution, of the one or more conjugated glycosaminoglycans, wherein the one or more conjugated glycosaminoglycans are a conjugated hyaluronic acid or a salt thereof.

22. The packaging system of claim 8, wherein the aqueous packaging solution further comprises one or more of a poloxamer and a poloxamine.

* * * * *